(12) United States Patent
Peterson

(10) Patent No.: US 7,632,963 B2
(45) Date of Patent: Dec. 15, 2009

(54) CRYSTAL OF (S)-(+)-2-(2-CHLOROPHENYL)-2-HYDROXY-ETHYL CARBAMATE

(75) Inventor: Matthew Peterson, Hopkinton, MA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 11/867,803

(22) Filed: Oct. 5, 2007

(65) Prior Publication Data

US 2008/0085930 A1   Apr. 10, 2008

Related U.S. Application Data

(60) Provisional application No. 60/828,392, filed on Oct. 6, 2007.

(51) Int. Cl.
 C07C 269/00    (2006.01)
 C07C 261/00    (2006.01)
(52) U.S. Cl. ............... 560/164; 514/483; 514/489
(58) Field of Classification Search ......... 560/164; 514/483, 489
See application file for complete search history.

(56) References Cited

U.S. PATENT DOCUMENTS

| | | | |
|---|---|---|---|
| 5,854,283 A * | 12/1998 | Choi et al. .............. | 514/483 |
| 6,103,759 A | 8/2000 | Choi et al. | |
| 6,627,642 B1 | 9/2003 | Kimura et al. | |
| 2004/0171679 A1* | 9/2004 | Plata-Salaman et al. ..... | 514/483 |
| 2006/0194873 A1* | 8/2006 | Choi et al. .............. | 514/483 |
| 2007/0021500 A1* | 1/2007 | Twyman et al. .......... | 514/483 |

FOREIGN PATENT DOCUMENTS

| WO | WO03053916 | * | 7/2003 |
|---|---|---|---|
| WO | WO 2005/169000 A | | 2/2005 |

OTHER PUBLICATIONS

Panagopoulou-Kaplani et al. Preparation and characterization of a new insoluble polymorphic form of glibenclamide. International Journal of Pharmaceutics, Feb. 15, 2000, vol. 195, Iss 1-2, pp. 239-246.

* cited by examiner

*Primary Examiner*—Sikarl A Witherspoon
(74) *Attorney, Agent, or Firm*—Peter Herridge

(57) ABSTRACT

The present invention relates to a novel crystal of (S)-(+)-2-(2-chlorophenyl)-2-hydroxy-ethyl carbamate, pharmaceutical compositions comprising this crystal and, and methods of making and using this crystal.

14 Claims, 3 Drawing Sheets

(I-a)

CRYSTAL OF (S)-(+)-2-(2-CHLOROPHENYL)-2-HYDROXY-ETHYL CARBAMATE

FIELD OF THE INVENTION

The present invention relates to a novel crystal of (S)-(+)-2-(2-chlorophenyl)-2-hydroxy-ethyl carbamate, pharmaceutical compositions comprising this crystal, and methods of making and using this crystal.

BACKGROUND OF THE INVENTION

Delivering an API to a patient requires more than just identifying a molecule and its use. An API must be formulated for delivery to a patient and this formulation (in addition to the API activity) is evaluated by regulatory agencies such as the US Food and Drug Administration (FDA) and the European Medicines Agency (EMEA). The FDA evaluates the formulation for, among other properties, delivery properties, stability, consistency, and manufacturing controls. An important factor in determining the properties of a particular formulation is the form of the API. APIs have been known to exist as amorphous forms, crystalline forms, polymorphs, hydrates and solvates. The forms for every API are different. While one particular API may be known to exist as a polymorph or a solvate, another API may be known to only exist in amorphous form. This form diversity is important because each different polymorph, solvate, hydrate or amorphous form may have different properties such as stability, solubility, and hygroscopicity.

Some forms of an API can be formulated into an FDA approvable formulation, while other forms lack the required properties to meet the high regulatory standards of the FDA. Even if a particular API can exist in more than one form suitable for formulation, different properties of an API form can affect the manufacturing process, shelf stability, route of administration, bioavailability and other important product characteristics. For example, the ability to improve or modulate stability or hygroscopicity can decrease manufacturing costs by reducing the need for humidity controlled chambers or reducing the need to package an API in humidity resistant packaging. In addition these same changes can increase product shelf stability thereby improving product distribution possibilities and affecting cost. In another example, one form of an API may have greater bioavailability than another form. Choosing the higher bioavailability form allows for a lower drug dose to be administered to a patient.

Thus, increasing the form diversity of a particular API increases opportunities to identify the ideal form for formulation. In addition, increasing form diversity increases the possibility of finding improved forms which can reduce manufacturing costs, increase shelf stability, offer new routes of administration, and offer new formulation options.

(S)-(+)-2-(2-chlorophenyl)-2-hydroxy-ethyl carbamate is useful for treating disorders of the central nervous system and is currently in clinical trials for such disorders. (S)-(+)-2-(2-chlorophenyl)-2-hydroxy-ethyl carbamate and methods of making this molecule are disclosed in U.S. Pat. No. 6,103,759. Applicants have discovered that (S)-(+)-2-(2-chlorophenyl)-2-hydroxy-ethyl carbamate can form a novel crystal possessing a distinct physical properties and a distinct crystal structure different than previously known forms of (S)-(+)-2-(2-chlorophenyl)-2-hydroxy-ethyl carbamate. This discovery increases opportunities for the identification of an improved formulation suitable for FDA approval and for the ability of affect manufacturing process, shelf stability, route of administration, bioavailability and other product characteristics.

SUMMARY OF THE INVENTION

The present invention relates to a Form β crystal of (S)-(+)-2-(2-chlorophenyl)-2-hydroxy-ethyl carbamate. The invention also provides for methods of making the novel Form β crystal. The invention also provides pharmaceutical compositions comprising this novel Form β crystal. Compositions and methods of the invention are useful in the treatment or prevention of a variety of diseases including, among others, convulsions, epilepsy, stroke, muscle spasms, neuropathic pain, and migraine.

DETAILED DESCRIPTION OF THE INVENTION

The present invention is directed to a novel Form β crystal of (S)-(+)-2-(2-chlorophenyl)-2-hydroxy-ethyl carbamate useful for treating and/or preventing central nervous system disorders such epilepsy, stroke, muscle spasms, neuropathic pain, and migraine.

Figure 1:
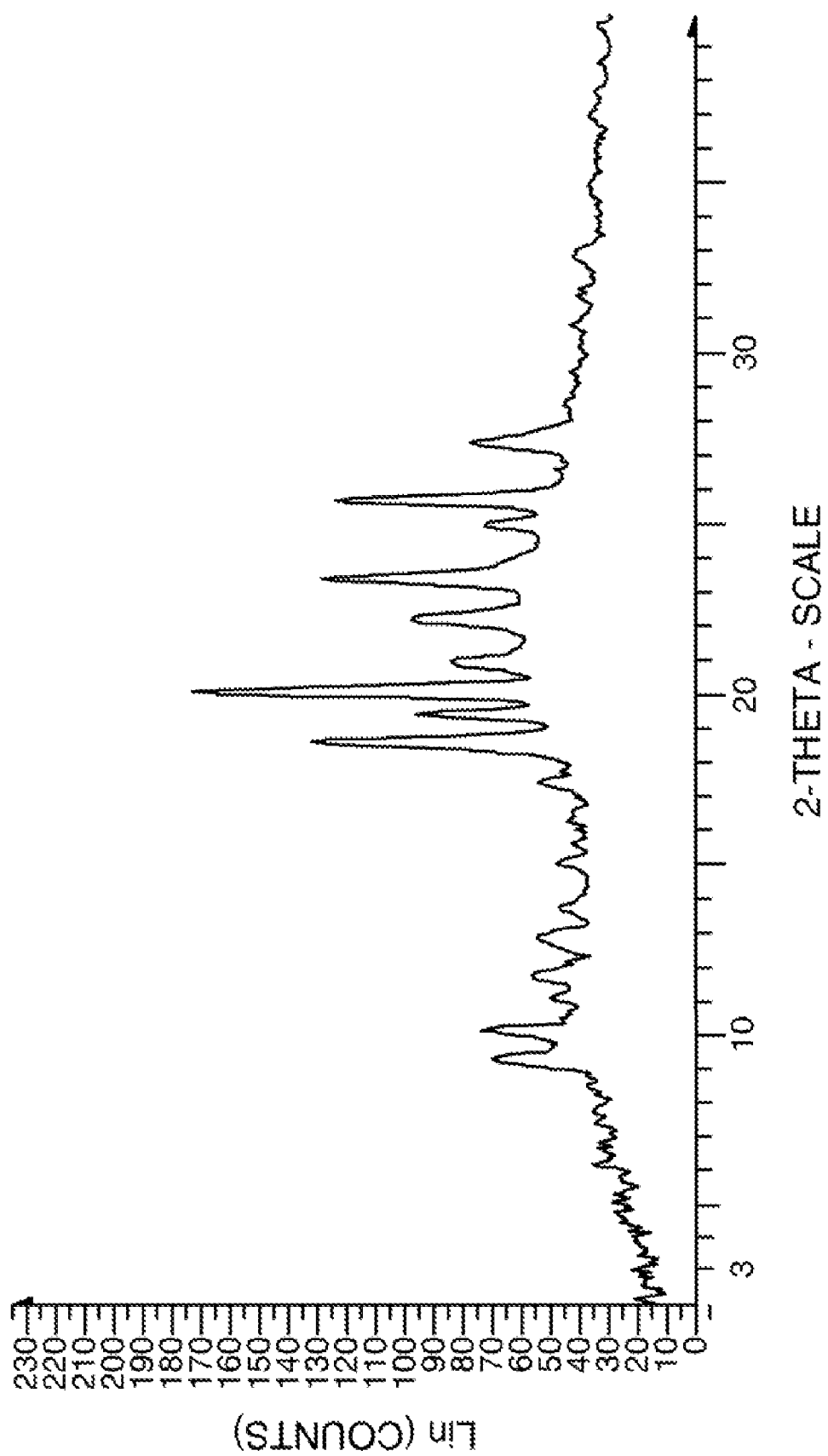
FIG. 1 illustrates powder X-ray diffraction (PXRD) measurements of a representative Form β crystal.
Figure 2:
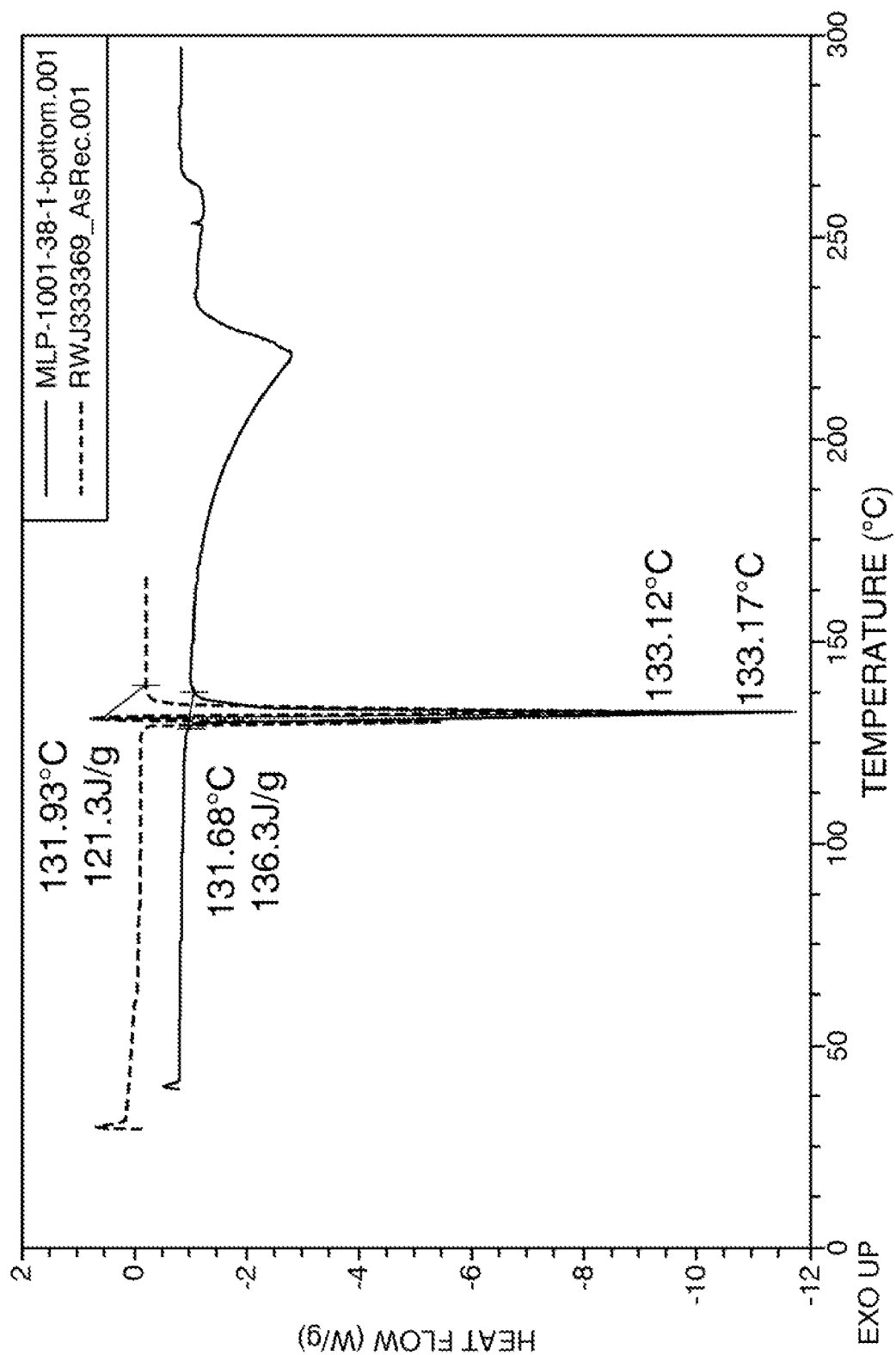
FIG. 2 illustrates differential scanning calorimetry (DSC) measurement of a representative Form β crystal.
Figure 3:
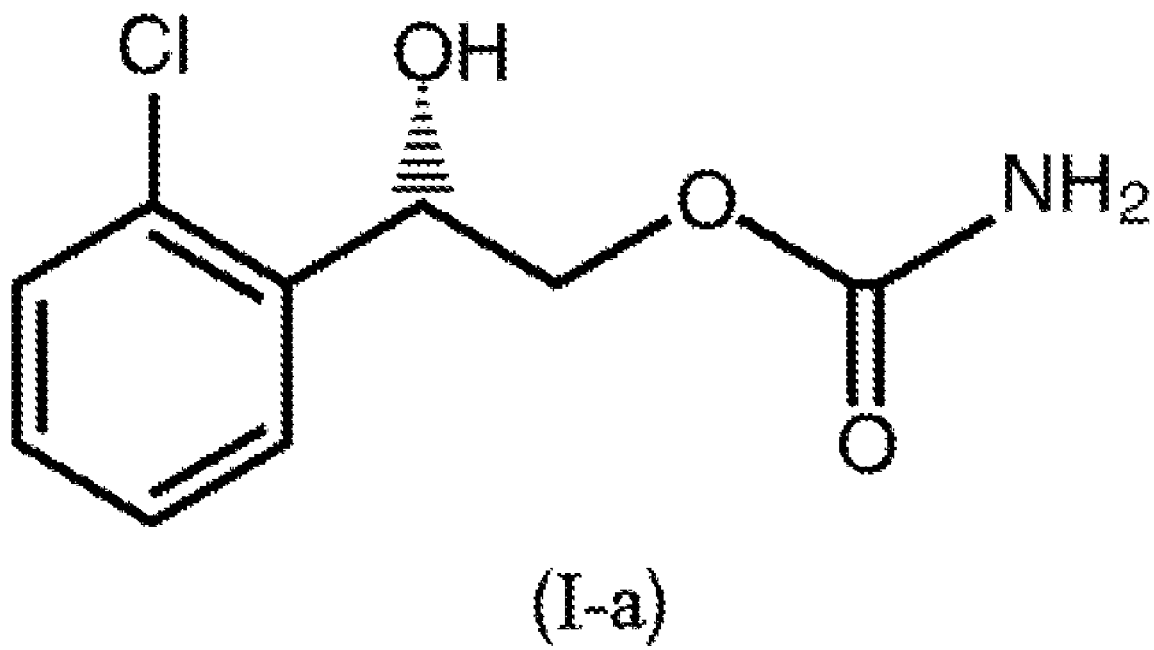
FIG. 3 is the molecular structure of the compound (S)-(+)-2-(2-chlorophenyl)-2-hydroxy-ethyl carbamate.

In a first embodiment, the present invention comprises a Form β crystal of (S)-(+)-2-(2-chlorophenyl)-2-hydroxy-ethyl carbamate. In one aspect of this invention, a Form β crystal is characterized by a powder X-ray diffraction pattern having one powder X-ray diffraction peak at about 10.0 degrees 2-theta. In another aspect of this invention, a Form β crystal is characterized by a powder X-ray diffraction pattern having powder X-ray diffraction peaks at about 10.0 and 11.7 degrees 2-theta. In a further aspect of this invention, a Form β crystal is characterized by a powder X-ray diffraction pattern having powder X-ray diffraction peaks at about 10.0, 11.7 and 12.8 degrees 2-theta. In a still further aspect of this invention, a Form β crystal is characterized by a powder X-ray diffraction pattern having powder X-ray diffraction peaks at about 10.0, 11.7, 12.8 and 19.4 degrees 2-theta. In another aspect of this invention, a Form β crystal is characterized by a powder X-ray diffraction pattern having powder X-ray diffraction peaks at about 10.0, 11.7, 12.8, 19.4, and 20.0 degrees 2-theta. In a further aspect of this invention, a Form β crystal is characterized by a powder X-ray diffraction pattern having powder X-ray diffraction peaks at about 10.0, 11.7, 12.8, 19.4, 20.0 and 22.2 degrees 2-theta. In a still further aspect of this invention, a Form β crystal is characterized by a powder X-ray diffraction pattern having powder X-ray diffraction peaks at about 10.0, 11.7, 12.8, 19.4, 20.0, 22.2 and 23.3 degrees 2-theta. In one aspect of this invention, a Form β crystal is characterized by a powder X-ray diffraction pattern having powder X-ray diffraction peaks at about 10.0, 11.7, 12.8, 19.4, 20.0, 22.2, 23.3 and 25.7 degrees 2-theta. In another aspect of this invention, a Form β crystal is characterized by a powder X-ray diffraction pattern having powder X-ray diffraction peaks at about 10.0, 11.7, 12.8, 19.4, 20.0, 22.2, 23.3, 25.7 and 27.3 degrees 2-theta. In another embodiment, a Form β crystal is characterized by a powder X-ray diffraction pattern that is substantially similar to the powder X-ray diffraction pattern of FIG. 1. In still another aspect of this invention, a Form β crystal is characterized by an endothermic transition at about 133 degrees C. In a further aspect of this invention, a Form β crystal is characterized by a differential scanning calorimetry (DSC) measurement substantially similar to the DSC in FIG. 2. In one aspect of this invention, a Form β crystal is substantially pure.

In another embodiment, the present invention comprises a method of treating a mammal suffering from a disease such as convulsions, epilepsy, stroke, muscle spasms, neuropathic pain, central nervous system disorders, and migraine, comprising administering to said mammal an effective amount of a Form β crystal of (S)-(+)-2-(2-chlorophenyl)-2-hydroxy-ethyl carbamate. In another embodiment, said mammal is a human.

Pharmaceutical dosage forms of a Form β crystal of (S)-(+)-2-(2-chlorophenyl)-2-hydroxy-ethyl carbamate can be administered in several ways including, but not limited to, oral administration. Oral pharmaceutical compositions and dosage forms are exemplary dosage forms. Optionally, the oral dosage form is a solid dosage form, such as a tablet, a caplet, a hard gelatin capsule, a starch capsule, a hydroxypropyl methylcellulose (HPMC) capsule, or a soft elastic gelatin capsule. Liquid dosage forms may also be provided by the present invention, including such non-limiting examples as a suspension, a solution, syrup, or an emulsion. In another embodiment, the present invention includes the preparation of a medicament comprising a Form β crystal of (S)-(+)-2-(2-chlorophenyl)-2-hydroxy-ethyl carbamate. A Form β crystal of (S)-(+)-2-(2-chlorophenyl)-2-hydroxy-ethyl carbamate can be administered by controlled- or delayed-release means.

Like the amounts and types of excipients, the amounts and specific type of active ingredient in a dosage form may differ depending on factors such as, but not limited to, the route by which it is to be administered to mammals. However, typical dosage forms of the invention comprise a Form β crystal of (S)-(+)-2-(2-chlorophenyl)-2-hydroxy-ethyl carbamate, in an amount of from about 0.10 mg to about 1.00 g, from about 0.2 mg to about 500.0 mg, or from about 1.0 mg to about 250.0 mg. Non-limiting examples include 0.2 mg, 0.50 mg, 0.75 mg, 1.0 mg, 1.2 mg, 1.5 mg, 2.0 mg, 3.0 mg, 5.0 mg, 7.0 mg, 10.0 mg, 25.0 mg, 50.0 mg, 100.0 mg, 250.0 mg, and 500.0 mg dosages. The dosages, however, may be varied depending upon the requirement of the patients, the severity of the condition being treated and the compound being employed. The use of either daily administration or post-periodic dosing may be employed.

The Form β crystal of (S)-(+)-2-(2-chlorophenyl)-2-hydroxy-ethyl carbamate of the present invention may also be used to prepare pharmaceutical dosage forms other than the oral dosage forms described above, such as topical dosage forms, parenteral dosage forms, transdermal dosage forms, and mucosal dosage forms. For example, such forms include creams, lotions, solutions, suspensions, emulsions, ointments, powders, patches, suppositories, and the like.

The Form β crystal of (S)-(+)-2-(2-chlorophenyl)-2-hydroxy-ethyl carbamate of the present invention can be characterized by the TGA or DSC data, or by any one, any two, any three, any four, any five, any six, any seven, any eight, any nine, any ten, or any single integer number of PXRD 2-theta angle peaks, or by any combination of the data acquired from the analytical techniques described above.

Although the invention has been described with respect to various embodiments, it should be realized this invention is also capable of a wide variety of further and other embodiments within the spirit and scope of the appended claims.

The Crystal of the Present Invention was Analyzed Using the Following Methods.

Differential Scanning Calorimetry

DSC analysis of each sample was performed using a Q1000 Differential Scanning Calorimeter (TA Instruments, New Castle, Del., U.S.A.), which uses Advantage for QW-Series, version 1.0.0.78, Thermal Advantage Release 2.0 (©2001 TA Instruments-Water LLC), with the following components: QDdv.exe version 1.0.0.78 build 78.2; RHBASE.DLL version 1.0.0.78 build 78.2; RHCOMM.DLL version 1.0.0.78 build 78.0; RHDLL.DLL version 1.0.0.78 build 78.1; an TGA.DLL version 1.0.0.78 build 78.1. In addition, the analysis software used was Universal Analysis 2000 for Windows 95/95/2000/NT, version 3.1E; Build 3.1.0.40 (©2001 TA Instruments-Water LLC).

For all of the DSC analyses, an aliquot of a sample was weighed into either a standard aluminum pan (Pan part #900786.091; lid part #900779.901) or a hermetic aluminum pan (Pan part #900793.901; lid part #900794.901 (TA Instruments, New Castle Del. USA)). Non-solvated samples were loaded into standard pans and were sealed either by crimping for dry samples or press fitting for wet samples (such as slurries). Solvated samples (including hydrates) were loaded into hermetic pans and hermetically sealed. The sample pan was loaded into the Q1000 Differential Scanning Calorimeter, which is equipped with an autosampler, and a thermogram was obtained by individually heating the same using the control software at a rate of 10° C./minute from $T_{min}$ (typically 30° C.) to $T_{max}$ (typically 300° C.) using an empty aluminum pan as a reference. Dry nitrogen (compressed nitrogen, grade 4.8 (BOC Gases, Murray Hill, N.J. USA)) was used as a sample purge gas and was set at a flow rate of 50 mL/minute. Thermal transitions were viewed and analyzed using the analysis software provided with the instrument.

Powder X-Ray Diffraction

Powder x-ray diffraction patterns were obtained using either a D/Max Rapid X-ray Diffractometer (Rigaku/MSC, The Woodlands, Tex., U.S.A.) or a Bruker D8 Discover with GADDS diffractometer (Bruker-AXS Inc., Madison, Wis., U.S.A.).

The D/Max Rapid X-ray Diffractometer was equipped with a copper source (Cu/$K_\alpha$1.5406 Å), manual x-y stage, and 0.3 mm collimator. A sample was loaded into a 0.3 mm quartz capillary tube (Charles Supper Company, Natick, Mass., U.S.A.) by sectioning off the closed end of the tube and tapping the small, open end of the capillary tube into a bed of the powdered sample or into the sediment of a slurried sample. The loaded capillary tube was mounted in a holder that was placed and fitted into the x-y stage. A diffractogram was acquired using control software (RINT Rapid Control Software, Rigaku Rapid/XRD, version 1.0.0 (©1999 Rigaku Co.)) under ambient conditions at a power setting of 46 kV at 40 mA in transmission mode, while oscillating about the omega-axis from 0-5 degrees at 1 degree/second, and spinning about the phi-axis over 360 degrees at 2 degrees/second. The exposure time was 15 minutes unless otherwise specified.

The diffractogram obtained was integrated of 2-theta from 2-40 degrees and chi (1 segment) from 0-36 degrees at a step size of 0.02 degrees using the cyllnt utility in the RINT Rapid display software (RINT Rapid display software, version 1.18 (Rigaku/MSC)) provided by Rigaku with the instrument. The dark counts value was set to 8 as per the system calibration by Rigaku. No normalization or omega, chi, or phi offsets were used for the integration.

The Bruker D8 Discover with GADDS Diffractometer was equipped with a copper source (Cu/K$_\alpha$1.5406 Å), computer controlled x-y-z stage, a 0.5 mm collimator and a Hi-Star area detector. Samples were loaded into a proprietary sample holder by tapping the sample holder into a powder bed and arraying the holders into a 96 position block. The block was then loaded onto the x-y-z stage and the sample positions were entered into the software. A diffractogram was acquired using control software (GADDS—General Area Detector Diffraction System, (Bruker, version 4.1.14 (©1997-2003 Bruker-AXS.)) under ambient conditions at a power setting of 46 kV at 40 mA in reflectance mode. The exposure time was 5 minutes unless otherwise specified.

The diffractogram obtained was integrated of 2-theta from 2-40 degrees and chi (1 segment) from 0-36 degrees at a step size of 0.02 degrees using the GADDS software.

The relative intensity of peaks in a diffractogram is not necessarily a limitation of the PXRD pattern because peak intensity can vary from sample to sample, e.g., due to crystalline impurities. Further, the angles of each peak can vary by about +/−0.1 degrees, or by about +/−0.05. The entire pattern or most of the pattern peaks may also shift by about +/−0.1 degrees to about +/−0.2 degrees due to differences in calibration, settings, and other variations from instrument to instrument and from operator to operator. All reported PXRD peaks in the Figures, Examples, and elsewhere herein are reported with an error of about ±0.1 degrees 2-theta. Unless otherwise noted, all diffractograms are obtained at about room temperature (about 24 degrees C. to about 25 degrees C.).

The following specific examples illustrate the present invention in more detail. They are, however, not intended to limit its scope in any manner.

EXAMPLES

Example 1

Preparation of a Form β Crystal 136.93 mg of (S)-(+)-2-(2-chlorophenyl)-2-hydroxy-ethyl carbamate was weighed and transferred into 10 ml conical flask and then sealed with a rubber septum. Nitrogen was used to purge the flask at room temperature for 1 hour through two needles input and output. Purging of the flask was continued while it was heated to 140° C. in an oil bath for one hour and then for another hour while it was heated to 170° C. after the sample was melted. The sample was cooled to room temperature by removing the flask from the oil bath. Some of the material had sublimed up into the top part of the flask. PXRD analysis indicted that this material was form A. The remaining material solidified in the bottom of the flask. PXRD analysis on the material is indicative of the new Form β crystal.

What is claimed is:

1. A Form β crystal- of (S)-(+)-2-(2-chlorophenyl)-2-hydroxy-ethyl carbamate wherein said crystal is characterized by a powder X-ray diffraction pattern having powder X-ray diffraction peaks at 10.0 and 11.7 degrees 2-theta.

2. The crystal of claim 1, wherein said crystal is characterized by a powder X-ray diffraction pattern having powder X-ray diffraction peaks at 10.0, 11.7 and 12.8 degrees 2-theta.

3. The crystal of claim 1, wherein said crystal is characterized by a powder X-ray diffraction pattern having powder X-ray diffraction peaks at 10.0, 11.7, 12.8 and 19.4 degrees 2-theta.

4. The crystal of claim 1, wherein said crystal is characterized by a powder X-ray diffraction pattern having powder X-ray diffraction peaks at 10.0, 11.7, 12.8, 19.4, and 20.0 degrees 2-theta.

5. The crystal of claim 1, wherein said crystal is characterized by a powder X-ray diffraction pattern having powder X-ray diffraction peaks at 10.0, 11.7, 12.8, 19.4, 20.0 and 22.2 degrees 2-theta.

6. The crystal of claim 1, wherein said crystal is characterized by a powder X-ray diffraction pattern having powder X-ray diffraction peaks at 10.0, 11.7, 12.8, 19.4, 20.0, 22.2 and 23.3 degrees 2-theta.

7. The crystal of claim 1, wherein said crystal is characterized by a powder X-ray diffraction pattern having powder X-ray diffraction peaks at 10.0, 11.7, 12.8, 19.4, 20.0, 22.2, 23.3 and 25.7 degrees 2-theta.

8. The crystal of claim 1, wherein said crystal is characterized by a powder X-ray diffraction pattern having powder X-ray diffraction peaks at 10.0, 11.7, 12.8, 19.4, 20.0, 22.2, 23.3, 25.7 and 27.3 degrees 2-theta.

9. The crystal of claim 1, wherein said crystal is characterized by a powder X-ray diffraction pattern that is identical to the powder X-ray diffraction pattern of FIG. 1.

10. The crystal of claim 1, wherein said crystal is characterized by an endothermic transition at 133 degrees C.

11. The crystal of claim 1, wherein said crystal is characterized by a differential scanning calorimetry measurement identical to the DSC in FIG. 2.

12. A pharmaceutical composition comprising the crystal of claim 1.

13. A method of treating a mammal suffering from convulsions, epilepsy, stroke, muscle spasms, neuropathic pain, central nervous system disorders, or migraine, comprising administering to said mammal an effective amount of a Form β crystal of (S)-(+)-2-(2-chlorophenyl)-2-hydroxy-ethyl carbamate.

14. The method of claim 13, wherein said mammal is a human.

* * * * *